United States Patent
Lee et al.

(10) Patent No.: US 9,957,348 B2
(45) Date of Patent: May 1, 2018

(54) PYRIDINIUIVI-BASED COMPOUND, EPOXY RESIN COMPOSITION COMPRISING SAME, AND APPARATUS MANUFACTURED USING SAME

(71) Applicant: SAMSUNG SDI CO., LTD., Yongin-si, Gyeonggi-do (KR)

(72) Inventors: Dong Hwan Lee, Uiwang-si (KR); Min Gyum Kim, Uiwang-si (KR); Jung Seob Kim, Uiwang-si (KR); Jin Min Cheon, Uiwang-si (KR); Hwan Sung Cheon, Uiwang-si (KR); Seung Han, Uiwang-si (KR)

(73) Assignee: Samsung SDI Co., Ltd., Yongin-si, Gyeonggi-do (KR)

( * ) Notice: Subject to any disclaimer, the term of this patent is extended or adjusted under 35 U.S.C. 154(b) by 107 days.

(21) Appl. No.: 15/111,337

(22) PCT Filed: May 9, 2014

(86) PCT No.: PCT/KR2014/004190
§ 371 (c)(1),
(2) Date: Jul. 13, 2016

(87) PCT Pub. No.: WO2015/108245
PCT Pub. Date: Jul. 23, 2015

(65) Prior Publication Data
US 2016/0333136 A1    Nov. 17, 2016

(30) Foreign Application Priority Data
Jan. 14, 2014 (KR) .......................... 10-2014-004794

(51) Int. Cl.
*C08G 59/40* (2006.01)
*C08L 63/00* (2006.01)
(Continued)

(52) U.S. Cl.
CPC .......... *C08G 59/4014* (2013.01); *B01J 31/02* (2013.01); *B01J 31/0271* (2013.01);
(Continued)

(58) Field of Classification Search
None
See application file for complete search history.

(56) References Cited

U.S. PATENT DOCUMENTS 4,990,587 A    2/1991    Shaw et al.

FOREIGN PATENT DOCUMENTS

JP    49014635 A  *  2/1974
JP    60-203628 A    10/1985
(Continued)

OTHER PUBLICATIONS

Nemcova et al., "Inhibition of steel corrosion in acid media by ammonium alkylxanthates," Werkstoffe und Korrosion, 19(12), pp. 1043-1049, (1968) (Year: 1968).*
(Continued)

*Primary Examiner* — Randy P Gulakowski
*Assistant Examiner* — Ha S Nguyen
(74) *Attorney, Agent, or Firm* — Lee & Morse, P.C.

(57) ABSTRACT

The present invention relates to a pyridinium-based compound of chemical formula 1, an epoxy resin composition comprising the same, and an apparatus manufactured by using the same.

12 Claims, 2 Drawing Sheets

(51) Int. Cl.

| | |
|---|---|
| *C08G 59/68* | (2006.01) |
| *C08G 59/24* | (2006.01) |
| *C08G 59/62* | (2006.01) |
| *C07D 213/30* | (2006.01) |
| *C07D 213/84* | (2006.01) |
| *H01L 23/29* | (2006.01) |
| *H01L 23/31* | (2006.01) |
| *B01J 31/02* | (2006.01) |
| *C07D 213/04* | (2006.01) |
| *C07D 213/85* | (2006.01) |

(52) U.S. Cl.
CPC ......... *C07D 213/04* (2013.01); *C07D 213/30* (2013.01); *C07D 213/84* (2013.01); *C07D 213/85* (2013.01); *C08G 59/245* (2013.01); *C08G 59/621* (2013.01); *C08G 59/686* (2013.01); *C08L 63/00* (2013.01); *H01L 23/295* (2013.01); *H01L 23/3121* (2013.01); *H01L 2224/16227* (2013.01); *H01L 2224/32225* (2013.01); *H01L 2224/73204* (2013.01); *H01L 2224/92125* (2013.01)

(56) References Cited

FOREIGN PATENT DOCUMENTS

| | | |
|---|---|---|
| KR | 2000-0024875 A | 5/2000 |
| KR | 10-2008-0024980 A | 3/2008 |

OTHER PUBLICATIONS

Wang et al., "The Redox Cleavage of the Sulfur-Sulfur Bond and Carbon-Sulfur Bond in Tetramethylthiuram Disulfide by N-Benzyl-1,4-dihydronicotinamide," Journal of Organic Chemistry (1971), 36(4), pp. 525-527 (Year: 1971).*

* cited by examiner

– PYRIDINIUM-BASED COMPOUND, EPOXY RESIN COMPOSITION COMPRISING SAME, AND APPARATUS MANUFACTURED USING SAME

CROSS REFERENCE TO RELATED APPLICATIONS

This is the U.S. national phase application based on PCT Application No. PCT/KR2014/004190, filed May 9, 2014, which is based on Korean Patent Application No. 10-2014-0004794, filed Jan. 14, 2014, the entire contents of all of which are hereby incorporated by reference.

TECHNICAL FIELD

The present invention relates to a pyridinium-based compound, an epoxy resin composition including the same, and an apparatus manufactured using the same.

BACKGROUND ART

Due to advantages such as low cost and suitability for mass production, transfer molding is widely used as a method of packaging semiconductor devices, such as integrated circuits (ICs) and large scale integration (LSI) chips, with epoxy resin compositions. In transfer molding, modification of epoxy resins or phenol resins as curing agents can lead to improvements in the characteristics and reliability of semiconductor devices. Such epoxy resin compositions include an epoxy resin, a curing agent, a curing catalyst, and the like.

Although imidazole catalysts and amine catalysts have generally been utilized as the curing catalyst, these catalysts exhibit a curing acceleration effect at low temperature. For example, when an epoxy resin is mixed with other components before curing, the epoxy resin composition is partially cured by heat generated from the mixture system or externally applied heat, and, after completion of mixing, the epoxy resin composition can be further cured during storage at room temperature. Such partial curing can cause the epoxy resin composition to exhibit reduction in viscosity and deterioration in fluidity. In addition, since such state change is not uniform within the epoxy resin composition, the composition is subject to local curing variation. This can cause deterioration in mechanical, electrical and chemical properties of a molded article in manufacture of the molded article from the thermosetting epoxy resin composition through curing at high temperature. Accordingly, since use of the curing accelerator requires precise control of mixing time of each component and strict management of storage at low temperature, transportation, and molding conditions, the epoxy resin composition becomes difficult to handle. Further, if the composition is curable at a wide temperature range, this can cause deterioration in productivity and processability.

In the related art, Korean Patent Publication No. 10-0290448 discloses an epoxy resin curing catalyst which is a carboxylate of a bicyclic amidine.

DISCLOSURE

Technical Problem

It is an aspect of the present invention to provide a pyridinium-based compound, which has low curing initiation temperature and thus can catalyze curing of an epoxy resin even at low temperature.

It is another aspect of the present invention to provide a pyridinium-based compound, which exhibits low rate of viscosity change and high storage stability to catalyze curing only at a desired curing temperature while not exhibiting any catalytic activity at other temperatures.

It is a further aspect of the present invention to provide a pyridinium-based compound, which has narrow temperature range in which curing of an epoxy resin can be achieved, thereby enhancing processability and productivity.

Technical Solution

In accordance with one aspect of the present invention, a pyridinium-based compound may be represented by Formula 1:

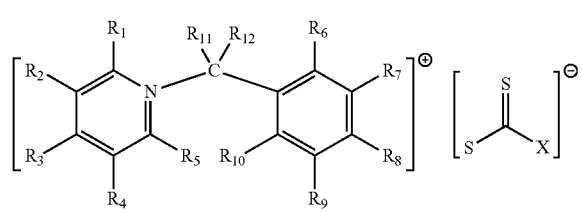

(where $R_1$, $R_2$, $R_3$, $R_4$, $R_5$, $R_6$, $R_7$, $R_8$, $R_9$, $R_{10}$, $R_{11}$, $R_{12}$, and X are the same as defined in the following detailed description).

In accordance with another aspect of the present invention, an epoxy resin composition may include an epoxy resin, a curing agent, and a curing catalyst, wherein the curing catalyst may include the pyridinium-based compound as set forth above.

In accordance with a further aspect of the present invention, an apparatus may be manufactured using the epoxy resin composition as set forth above.

Advantageous Effects

The present invention provides a pyridinium-based compound, which can catalyze curing of an epoxy resin even at low temperature. In addition, the present invention provides a pyridinium-based compound, which exhibits high storage stability to catalyze curing only at a desired curing temperature while not exhibiting any catalytic activity at other temperatures. Further, the present invention provides a pyridinium-based compound, which has narrow temperature range in which curing of an epoxy resin can be achieved, thereby enhancing processability and productivity.

BEST MODE

Figure 1:
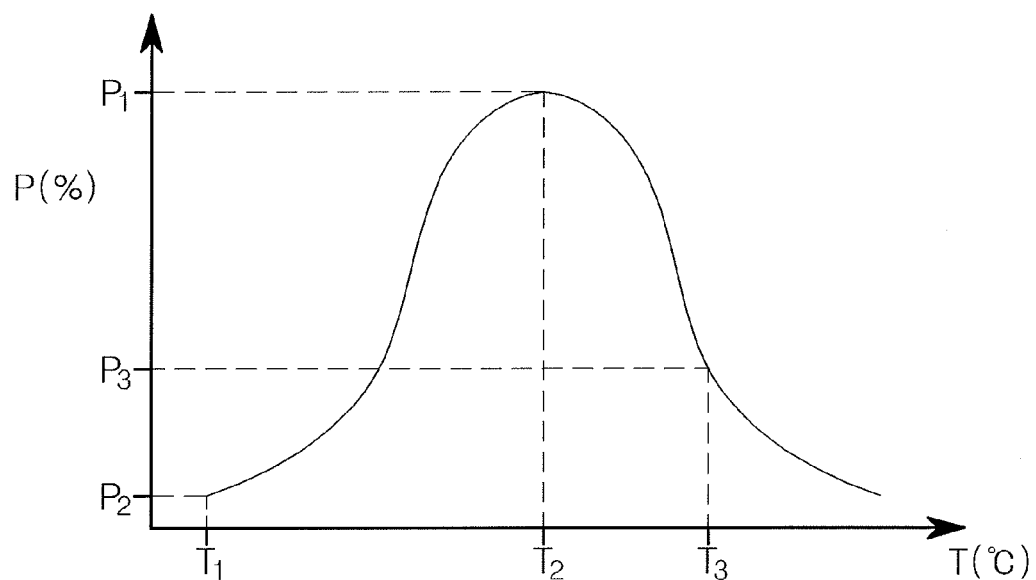
FIG. 1 is a schematic diagram showing curing rate P as a function of curing temperature (° C.) for an epoxy resin composition according to one embodiment of the present invention.

Hereinafter, embodiments of the present invention will be described in detail with reference to the accompanying drawings so as to be easily practiced by those skilled in the art. It should be understood that the present invention is not limited to the following embodiments and may be embodied in different ways. In the drawings, portions irrelevant to the description will be omitted for clarity. Like components will be denoted by like reference numerals throughout the specification.

One aspect of the present invention relates to a pyridinium-based compound. The pyridinium-based compound may be represented by Formula 1:

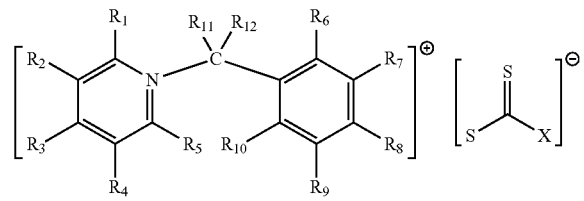

(where $R_1$, $R_2$, $R_3$, $R_4$, $R_5$, $R_6$, $R_7$, $R_8$, $R_9$, and $R_{10}$ are each independently hydrogen, a hydroxyl group, an amino group (—$NH_2$), a nitro group (—$NO_2$), a cyano group (—CN), a $C_1$ to $C_{10}$ alkyl group, a $C_6$ to $C_{20}$ aryl group, a $C_1$ to $C_{10}$ alkoxy group, a $C_3$ to $C_{10}$ cycloalkyl group, R—C(=O)—* (where R is a $C_1$ to $C_{10}$ alkyl group, and * is a binding site between elements), or R—$SO_2$—* (where * is a binding site between elements, and R' is a $C_1$ to $C_{10}$ alkyl group or $C_6$ to $C_{20}$ aryl group);

$R_{11}$, $R_{12}$ are each independently hydrogen, a $C_1$ to $C_{10}$ alkyl group, a $C_6$ to $C_{20}$ aryl group, or a hydroxyl group; and X is *—$NR_aR_b$ (where $R_a$ and $R_b$ are each independently hydrogen, a $C_1$ to $C_{10}$ alkyl group, a $C_6$ to $C_{20}$ aryl group, a $C_1$ to $C_{10}$ alkoxy group, a $C_6$ to $C_{20}$ aryloxy group, or a $C_7$ to $C_{20}$ arylalkyl group, and * is a binding site between elements) or *—$OR_c$ (where $R_c$ is hydrogen, a $C_1$ to $C_{10}$ alkyl group, a $C_6$ to $C_{20}$ aryl group, a $C_1$ to $C_{10}$ alkoxy group, a $C_6$ to $C_{20}$ aryloxy group, or a $C_7$ to $C_{20}$ arylalkyl group, and * is a binding site between elements).

Specifically, $R_1$, $R_2$, $R_3$, $R_4$, $R_5$, $R_6$, $R_7$, $R_8$, $R_9$, and $R_{10}$ may each independently be hydrogen, a $C_1$ to $C_5$ alkoxy group, a cyano group, or a nitro group; $R_{11}$ and $R_{12}$ may be hydrogen; and X may be *—$NR_aR_b$ wherein $R_a$ and $R_b$ are each independently hydrogen, a $C_1$ to $C_5$ alkyl group, or a $C_7$ to $C_{10}$ arylalkyl group or *—$OR_c$ wherein $R_c$ is a $C_1$ to $C_5$ alkyl group.

The compound represented by Formula 1 may decompose and generates pyridinium cations and dithio anions at about 80° C. to about 130° C. upon application of external energy such as heat. Since pyridinium cations can catalyze curing of an epoxy resin, the compound represented by Formula 1 may be used as a latent curing catalyst for an epoxy resin composition including an epoxy resin, a curing agent, and the like.

In particular, pyridinium cations may allow an aromatic group constituting the pyridinium-based compound to contain electron donating groups and thus enhance reactivity of the epoxy resin composition at low temperature to lower the curing initiation temperature of the resin composition, thereby providing excellent low temperature curability to the resin composition, and dithio anions allow the epoxy resin composition to be completely cured even in a narrow temperature range, thereby improving processability of the epoxy resin composition. As used herein, "curing initiation temperature" refers to a temperature at which the inclination of the heat of reaction curve at the peak temperature meets the line connecting the temperature at which curing of an epoxy resin composition starts and the temperature at which curing of the epoxy resin composition is complete, when heat of reaction of the epoxy resin composition is measured by differential scanning calorimetry (DSC) after heating the epoxy resin composition to about 250° C. at a heating rate of about 10° C./min subsequent to maintaining the resin composition at an initial temperature of about 30° C. for about 1 minute, and may range, for example, from about 80° C. to about 130° C., specifically about 80° C. to about 100° C.

FIG. 1 is a schematic diagram showing curing rate P as a function of curing temperature for an epoxy resin composition including a pyridinium salt according to one embodiment of the present invention. In FIG. 1, T of the x-axis refers to temperature (° C.), and P of the y-axis refers to curing rate (%).

Referring to FIG. 1, the curing initiation temperature ($T_1$, curing rate $P_2$: about 5%) may range from about 80° C. to about 130° C., specifically about 90° C. to about 120° C., specifically about 80° C. to about 100° C.; the temperature $T_2$ at which curing rate P reaches its peak (curing rate $P_1$: about 30% to about 80%) may range from about 120° C. to about 180° C.; and the temperature at which curing is complete may range ($T_3$, curing rate $P_3$: about 40% or higher) from about 130° C. to about 200° C. The curing rate P may be measured by any typical method, for example, by DSC or using a Shore-D durometer. As such, the compound represented by Formula 1 may be used as a latent curing catalyst which can lower curing initiation temperature and narrow the temperature range in which curing is completed.

The compound represented by Formula 1 can catalyze curing of an epoxy resin and a curing agent, and secures storage stability. As used herein, the term "storage stability" refers to the ability to catalyze curing only at a desired curing temperature while not exhibiting any catalytic activity at other temperatures. As a result, it is possible to store the epoxy resin composition for a long time without causing viscosity change. Generally, curing reaction can cause increase in viscosity and deterioration in flowability when the epoxy resin composition is liquid, and can exhibit viscosity when the epoxy resin composition is solid. An epoxy resin composition including the compound represented by Formula 1 may have a curing initiation temperature of about 80° C. to about 130° C. and a curing peak temperature of about 120° C. to about 180° C., as measured by differential scanning calorimetry (DSC). Within this range, the epoxy resin composition has low curing initiation temperature and low curing peak temperature, and thus can have low temperature curability.

The compound represented by Formula 1 may be a salt type compound.

As such, the compound represented by Formula 1 may be used as a curing catalyst for an epoxy resin composition including an epoxy resin and a curing agent. In one embodiment, the epoxy resin may have two or more epoxy groups per molecule, and examples of the epoxy resin may include bisphenol A type epoxy resins, bisphenol F type epoxy resins, phenol novolac type epoxy resins, tert-butyl catechol type epoxy resins, naphthalene type epoxy resins, glycidyl amine type epoxy resins, cresol novolac type epoxy resins, biphenyl type epoxy resins, linear aliphatic epoxy resins, alicyclic epoxy resins, heterocyclic epoxy resins, Spiro ring-containing epoxy resins, cyclohexane dimethanol type epoxy resins, trimethylol type epoxy resins, and halogenated epoxy resins. These epoxy resins may be used alone or in combination thereof. For example, the epoxy resin may have two or more epoxy groups and one or more hydroxyl groups per molecule. The epoxy resin may include at least one of a solid phase epoxy resin and a liquid phase epoxy resin, and a solid phase epoxy resin is preferably used.

In one embodiment, the curing agent may include phenolaralkyl type phenol resins, phenol novolac type phenol resins, xyloc type phenol resins, cresol novolac type phenol resins, naphthol type phenol resins, terpene type phenol resins, multifunctional phenol resins, dicyclopentadiene-based phenol resins, novolac type phenol resins synthesized from bisphenol A and resol, polyhydric phenol compounds including tris(hydroxyphenyl)methane and dihydroxybiphenyl, acid anhydrides including maleic anhydride and phthalic anhydride, and aromatic amines including meta-phenylenediamine, diaminodiphenylmethane, diaminodiphenylsulfone, and the like. For example, the curing agent may be a phenol resin having one or more hydroxyl groups.

The compound represented by Formula 1 may be present in an amount of about 0.01 wt % to about 5 wt %, for example, about 0.02 wt % to about 1.5 wt %, for example, about 0.05 wt % to about 1.5 wt % in the epoxy resin composition. Within this range, the epoxy resin composition can secure flowability without delaying time for curing reaction.

The compound represented by Formula 1 may be prepared by a typical method. For example, the compound represented by Formula 1 may be prepared by reacting a pyridinium cationic compound represented by Formula 2 with a compound represented by Formula 3:

<Formula 2>

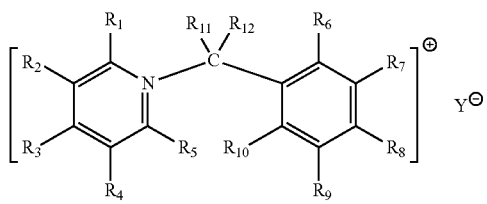

(where $R_1$, $R_2$, $R_3$, $R_4$, $R_5$, $R_6$, $R_7$, $R_8$, $R_9$, $R_{10}$, $R_{11}$, and $R_{12}$ are as defined in Formula 1, and Y is halogen)

<Formula 3>

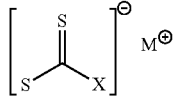

(where X is as defined in Formula 1, and M is an alkali metal).

Halogen is fluorine, chlorine, bromine, or iodine, and the alkali metal is lithium, sodium, rubidium, cesium, or francium.

The pyridinium cationic compound may be prepared by combining a pyridine compound with an alkyl halide, an aryl halide, an aralkyl halide, or the like in the presence of a solvent or may be a pyridinium cation-containing salt, and the compound represented by Formula 3 may be a dithiocarbamate anion-containing salt or a xanthate anion-containing salt. The pyridine compound may include pyridine and the like. The compound represented by Formula 3 may include anionic alkali metal salts such as diethyldithiocarbamate, dibutyldithiocarbamate, di benzyldithiocarbamate, or isopropyl xanthate.

Reaction between the compound represented by Formula 2 and the compound represented by Formula 3 may be performed in an organic solvent such as methylene chloride, acetonitrile, N,N-dimethylformamide, and toluene at a temperature of about 10° C. to about 100° C., for example, about 20° C. to about 80° C., for about 1 to 30 hours, for example, for about 10 to 24 hours. The pyridinium cation-containing compound (compound represented by Formula 2) and the compound represented by Formula 3 may be reacted in a mole ratio of about 1:0.9 to about 1:1.5. Within this range, synthesis of a material containing pyridinium cations and dithiocarbamate anions is possible. The reaction may be performed by mixing the pyridinium cation-containing compound and the compound represented by Formula 4, or may be performed by combining the pyridinium cation-containing compound with an alkyl halide, an aryl halide, an aralkyl halide, or the like to prepare the pyridinium cation-containing compound, followed by adding the compound represented by Formula 3 thereto in-situ without an additional separation process.

Another aspect of the present invention relates to an epoxy resin composition. The epoxy resin composition may include the pyridinium-based compound, an epoxy resin, and a curing agent.

The epoxy resin may include bisphenol A type epoxy resins, bisphenol F type epoxy resins, phenol novolac type epoxy resins, tert-butyl catechol type epoxy resins, naphthalene type epoxy resins, glycidyl amine type epoxy resins, cresol novolac type epoxy resins, biphenyl type epoxy resins, linear aliphatic epoxy resins, alicyclic epoxy resins, heterocyclic epoxy resins, Spiro ring-containing epoxy resins, cyclohexane dimethanol type epoxy resins, trimethylol type epoxy resins, and halogenated epoxy resins. These epoxy resins may be used alone or in combination thereof.

In one embodiment, the epoxy resin may be a biphenyl type epoxy resin represented by Formula 4:

<Formula 4>

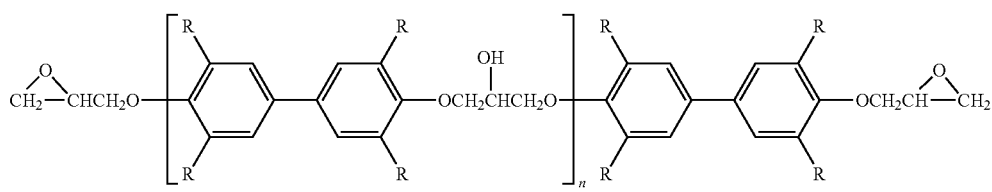

(where R is a $C_1$ to $C_4$ alkyl group, and n ranges from 0 to 7 on average.)

The epoxy resin may be present, in terms of solid content, in an amount of about 1 wt % to about 90 wt %, for example, about 2 wt % to about 17 wt %, for example, about 3 wt % to about 15 wt %, for example, about 3 wt % to about 12 wt %, in the composition. Within this range, the composition can secure curability.

The curing agent may include phenolaralkyl type phenol resins, phenol novolac type phenol resins, xyloc type phenol resins, cresol novolac type phenol resins, naphthol type phenol resins, terpene type phenol resins, multifunctional phenol resins, dicyclopentadiene-based phenol resins, novolac type phenol resins synthesized from bisphenol A and resol, polyhydric phenol compounds including tris(hydroxyphenyl)methane and dihydroxybiphenyl, acid anhydrides including maleic anhydride and phthalic anhydride, and aromatic amines including meta-phenylenediamine, diaminodiphenylmethane, diaminodiphenylsulfone, and the like.

In one embodiment, the curing agent may be a xyloc type phenol resin represented by Formula 5 or a phenolaralkyl type phenol resin represented by Formula 6:

about 100 wt % of a fused silica mixture based on the total weight of the inorganic fillers, wherein the fused silica mixture includes about 50 wt % to about 99 wt % of spherical fused silica having an average particle diameter of about 5 μm to about 30 pun and about 1 wt % to about 50 wt % of spherical fused silica having an average particle diameter of about 0.001 μm to about 1 μm. The inorganic fillers may also be adjusted to a maximum particle diameter of about 45 μm, about 55 μm or about 75 μm, depending upon application of the epoxy resin composition. Although the spherical fused silica may include conductive carbon as a foreign substance on the surface of silica, it is essential for the spherical fused silica to incorporate a smaller amount of polar foreign substances.

The inorganic fillers may be present in an appropriate amount depending upon desired physical properties of the epoxy resin composition, for example, moldability, low-stress properties, and high-temperature strength. Specifically, the inorganic fillers may be present in an amount of about 70 wt % to about 95 wt %, for example, about 70% to about 90 wt %, based on the total weight of the epoxy resin composition. Within this range, the epoxy resin composition can secure good flame resistance, flowability, and reliability.

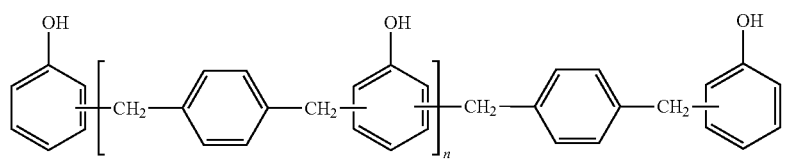

<Formula 5>

(where n ranges from 0 to 7 on average.)

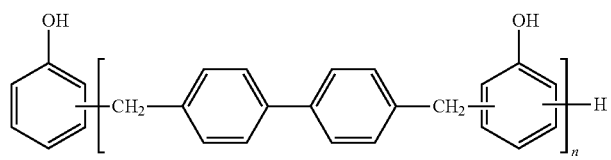

<Formula 6>

(where n ranges from 1 to 7 on average.)

The curing agent may be present, in terms of solid content, in an amount of about 0.1 wt % to about 90 wt %, for example, about 5 wt % to about 13 wt %, for example, about 1 wt % to about 10 wt %, for example, about 2 wt % to 8 wt % in the composition. Within this range, the composition can secure curability.

The epoxy resin composition may further include inorganic fillers. The epoxy resin composition including inorganic fillers may be used for encapsulating a semiconductor device. The inorganic fillers are used to improve mechanical properties of the epoxy resin composition while reducing stress thereof. Examples of the inorganic fillers include at least one of fused silica, crystalline silica, calcium carbonate, magnesium carbonate, alumina, magnesia, clay, talc, calcium silicate, titanium oxide, antimony oxide, and glass fibers.

Fused silica having a low coefficient of linear expansion is preferred in terms of stress reduction. The fused silica refers to amorphous silica having a specific gravity of 2.3 or less. The fused silica may be prepared by melting crystalline silica or may include amorphous silica products synthesized from various raw materials. Although the shape and particle diameter of the fused silica are not particularly limited, it is desirable that the inorganic fillers include about 40 wt % to The epoxy resin composition may further include a non-pyridinium curing catalyst which does not contain pyridinium The non-pyridinium curing catalyst may include tertiary amines, organometallic compounds, organophosphorus compounds, imidazole, boron compounds, and the like. Examples of tertiary amines include benzyldimethylamine, triethanolamine, triethylenediamine, diethylaminoethanol, tri(dimethylaminomethyl)phenol, 2,2-(dimethylaminomethyl)phenol, 2,4,6-tris(diaminomethyl)phenol, tri-2-ethyl hexanoate, and the like. Examples of organometallic compounds include chromium acetylacetonate, zinc acetylacetonate, nickel acetylacetonate, and the like. Examples of organophosphorus compounds include tris-4-methoxyphosphine, triphenylphosphine, triphenylphosphine triphenylborane, triphenylphosphine-1,4-benzoquinone adducts, and the like. Examples of imidazole include 2-methylimidazole, 2-phenylimidazole, 2-aminoimidazole, 2-methyl-1-vinylimidazole, 2-ethyl-4-methylimidazole, 2-heptadecyl imidazole, and the like. Examples of boron compounds include triphenylphosphine tetraphenyl borate, tetraphenyl borate, trifluoroborane-n-hexylamine, trifluoroborane monoethylamine, tetrafluoroborane triethylamine, tetrafluoroboraneamine, and the like. In addition, it is possible to use 1,5-diazabicyclo[4.3.0]non-5-ene (DBN), 1,8-diazabicyclo

[5.4.0]undec-7-ene (DBU), phenol novolac resin salt, and the like. Particularly, the organophosphorus compounds, the boron compounds, and the amine or imidazole curing accelerators may be used alone or in combination. In addition, the curing catalyst may be used in the form of adducts obtained by pre-reacting the curing catalyst with the epoxy resin or the curing agent.

The pyridinium-based compound according to the present invention may be present in an amount of about 10 wt % to about 100 wt %, for example, about 10 wt % to about 70 wt %, based on the total weight of the curing catalyst. Within this range, the epoxy resin composition can secure flowability without delaying time for curing reaction.

The curing catalyst may be present in an amount of about 0.01 wt % to about 10 wt %, for example, about 0.01 wt % to about 5 wt %, for example, about 0.01 wt % to about 3 wt %, for example, about 0.05 wt % to about 1.0 wt %, in the epoxy resin composition. Within this range, the epoxy resin composition can secure flowability without delaying time for curing reaction.

The epoxy resin composition may further include a typical additive. In one embodiment, the additive may include at least one of a coupling agent, a release agent, a stress reliever, a crosslinking enhancer, a leveling agent, and a coloring agent.

The coupling agent may include at least one selected from the group consisting of epoxysilane, aminosilane, mercaptosilane, alkylsilane, and alkoxysilane, without being limited thereto. The coupling agent may be present in an amount of about 0.1 wt % to about 1 wt % in the epoxy resin composition.

The release agent may include at least one selected from the group consisting of paraffin wax, ester wax, higher fatty acids, metal salts of higher fatty acids, natural fatty acids, and natural fatty acid metal salts. The release agent may be present in an amount of about 0.1 wt % to about 1 wt % in the epoxy resin composition.

The stress reliever may include at least one selected from the group consisting of modified silicone oil, silicone elastomers, silicone powder, and silicone resin, without being limited thereto. The stress reliever may be optionally present in an amount of about 6.5 wt % or less, for example, about 1 wt % or less, for example, about 0.1 wt % to about 1 wt % in the epoxy resin composition. As the modified silicone oil, any silicone polymers having good heat resistance may be used. The modified silicone oil may include about 0.05 wt % to about 1.5 wt % of a silicone oil mixture based on the total weight of the epoxy resin composition, wherein the mixture includes at least one selected from the group consisting of silicone oil having an epoxy functional group, silicone oil having an amine functional group, silicone oil having a carboxyl functional group, and a combination thereof. However, if the amount of the silicone oil is greater than about 1.5 wt %, surface contamination occurs easily and lengthy resin bleed can be encountered, whereas if the amount of the silicone oil is less than 0.05 wt %, there can be a problem in that sufficiently low modulus of elasticity cannot be obtained. In addition, the silicone powder having an average particle diameter of about 15 μm or less is particularly preferred in that the powder does not deteriorate moldability. The silicone powder may be optionally present in an amount of about 5 wt % or less, for example, about 0.1 wt % to about 5 wt %, based on the total weight of the epoxy resin composition.

The additive may be present in an amount of about 0.1 wt % to about 10 wt %, for example, about 0.1 wt % to about 3 wt %, in the epoxy resin composition.

The epoxy resin composition has high storage stability by including the compound represented by Formula 1 and thus is not cured at predetermined ranges of time and temperature, whereby viscosity of the epoxy resin composition shows only slight change. In one embodiment, the epoxy resin composition may have a rate of viscosity change of about 13% or less, for example, about 0 wt % to about 13%, for example, about 0 wt % to about 9% or less as calculated according to Equation 1:

$$\text{Rate of viscosity change} = |B-A|/A \times 100 \qquad \text{<Equation 1>}$$

(where A is the viscosity (unit: cPs) of the epoxy resin composition as measured at about 25° C., and B is the viscosity (unit: cPs) of the epoxy resin composition as measured at about 25° C. after leaving the epoxy resin composition at about 25° C. for about 24 hours).

Within this range, since the epoxy resin composition exhibits high storage stability, curing of the epoxy resin composition is catalyzed only at a desired curing temperature, and catalytic activity is not exhibited at other curing temperatures. In addition, the epoxy resin composition does not suffer deterioration in moldability due to poor flowability when undergoing curing reaction at high temperature, thereby preventing degradation in mechanical, electrical, and chemical properties of a molded product manufactured using the resin composition. Specifically, A may range from about 100 cPs to about 3000 cPs, and B ranges from about 100 cPs to about 3000 cPs.

The epoxy resin composition may have a flow length of about 30 to 80 inches, specifically about 63 to 80 inches as measured using a transfer molding press at about 175° C. under a load of about 70 kgf/cm² in accordance with EMMI-1-66. Within this range, the epoxy resin composition can be used for desired applications.

The epoxy resin composition may have a curing shrinkage of less than about 0.4%, for example, about 0.01% to about 0.39%, as calculated according to Equation 2:

$$\text{Curing shrinkage} = |C-D|/C \times 100 \qquad \text{<Equation 2>}$$

(where C is the length of a specimen obtained by transfer molding of the epoxy resin composition at about 175° C. under a load of about 70 kgf/cm², and D is the length of the specimen after post-curing the specimen at about 170° C. to about 180° C. for about 4 hours and cooling). Within this range, curing shrinkage is low and the epoxy resin composition can be used for desired applications.

The epoxy resin composition according to the present invention can be used in a broad range of applications requiring such an epoxy resin composition in encapsulation of semiconductor devices, adhesive films, insulating resin sheets such as prepregs and the like, circuit substrates, solder resists, underfills, die bonding materials, and component replenishing resins, without being limited thereto.

(1) Encapsulation of Semiconductor Device

The epoxy resin composition according to the present invention may be used to encapsulate a semiconductor device, and include an epoxy resin, a curing agent, a pyridinium salt-containing curing catalyst, inorganic fillers, and additives.

In one embodiment, the epoxy resin may be present in an amount of about 2 wt % to about 17 wt %, for example, about 3 wt % to about 12 wt % in the composition, and within this range, the epoxy resin composition can exhibit excellent flowability, flame retardancy, and reliability. The pyridinium-based compound-containing curing catalyst may be present in an amount of about 0.01 wt % to about 5 wt %, for example, about 0.05 wt % to about 1.5 wt % in the composition, and within this range, the epoxy resin composition can exhibit excellent reliability due to reduction in the amount of unreacted epoxy groups and phenolic hydroxyl groups. The curing agent may be present in an amount of about 0.5 wt % to about 13 wt %, for example, about 2 wt % to about 8 wt % in the composition, and within this range, the epoxy resin composition can exhibit excellent reliability due to reduction in the amount of unreacted epoxy groups and phenolic hydroxyl groups. The inorganic fillers may be present in an amount of about 70 wt % to about 95 wt %, for example, about 75 wt % to about 92 wt % in the composition, and within this range, the epoxy resin composition can exhibit excellent flowability, flame retardancy, and reliability. The additives may be present in an amount of about 0.1 wt % to about 10 wt %, for example, about 0.1 wt % to about 3 wt % in the composition.

The epoxy resin in the epoxy resin composition may be used alone or in the form of adducts, such as a melt master batch, obtained by pre-reaction of the epoxy resin with additives such as a curing agent, a curing catalyst, a release agent, a coupling agent, and a stress reliever. Although the method of preparing the epoxy resin composition is not particularly limited, the epoxy resin composition may be prepared by a process in which components of the composition are uniformly mixed using a Henschel mixer or a Lödige mixer, followed by melt kneading using a roll mill or a kneader at about 90° C. to about 120° C., and then cooling and pulverizing.

As a method for encapsulating a semiconductor device using the epoxy resin composition obtained according to the present invention, low-pressure transfer molding may be generally used. However, it should be understood that injection molding or casting may also be employed for molding of the epoxy resin composition. The semiconductor device that can be fabricated by such a molding process may include a copper lead frame, an iron lead frame, an iron lead frame pre-plated with at least one metal selected from among nickel, copper and palladium, or an organic laminate frame.

(2) Adhesive Film

The epoxy resin composition may be used as an adhesive film for a printed wiring board by applying the epoxy resin composition to a support film, followed by curing. An adhesive film may be prepared by a typical method known in the art, for example, a process wherein the epoxy resin composition is dissolved in an organic solvent, and the dissolved composition is coated onto a support film, which is a support, followed by drying the organic solvent through heating or hot air blasting. As the organic solvent, ketones such as acetone or methylethyl ketone; acetic acid esters such as ethyl acetate or butyl acetate; carbitols such as cellosolve or butyl carbitol; aromatic hydrocarbons such as toluene; and amide solvents such as dimethylformamide may be used. These may be used alone or in combination thereof. Although drying conditions are not particularly limited, the organic solvent may be dried at about 50° C. to about 100° C. for about 1 to 10 minutes such that the organic solvent can be present in an amount of about 10 wt % or less in the coating layer. As the support film, polyolefins such as polyethylene or polypropylene, polyesters such as polyethylene terephthalate, polycarbonate, polyimide, and the like may be used. The support film may have a thickness of about 10 μm to about 150 μm.

(3) Prepreg

The epoxy resin composition may be used as a prepreg by impregnating a sheet-like reinforcement substrate with the epoxy resin composition, followed by semi-curing through heating. The reinforcement substrate may include any suitable fibers generally used for prepregs, such as glass cloths or aramid fibers, without limitation.

Although the method of preparing the epoxy resin composition is not particularly limited, the epoxy resin composition may be prepared by a process wherein components of the composition are uniformly mixed using a Henschel mixer or Lödige mixer, followed by melt kneading using a roll mill or a kneader at about 90° C. to about 120° C., and then cooling and pulverizing. As a method for encapsulating a semiconductor device using the epoxy resin composition obtained according to the present invention, low-pressure transfer molding may be generally used. However, it should be understood that injection molding or casting may also be employed for molding of the epoxy resin composition. The semiconductor device that can be fabricated by such a molding process may include a copper lead frame, an iron lead frame, an iron lead frame pre-plated with at least one metal selected from among nickel, copper and palladium, or an organic laminate frame.

A further aspect of the invention relates to an apparatus manufactured using the epoxy resin composition as set forth above. For example, the apparatus may include a semiconductor device encapsulated with the epoxy resin composition and a multilayer wiring board including an adhesive film formed of the epoxy resin composition.

Figure 2:
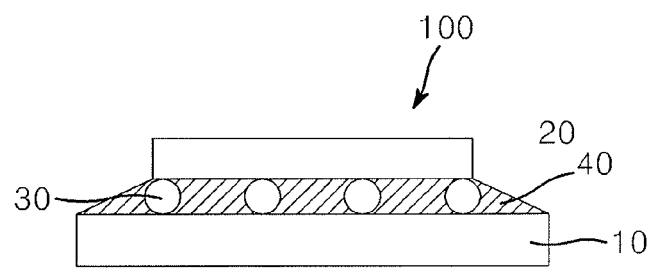
FIG. 2 is a sectional view of a semiconductor device according to one embodiment of the present invention.

FIG. 2 is a sectional view of a semiconductor device according to one embodiment of the present invention. Referring to FIG. 2, a semiconductor device 100 according to one embodiment includes a wiring board 10, bumps 30 formed on the wiring board 10, and a semiconductor chip 20 formed on the bumps 30, wherein a gap between the wiring board 10 and the semiconductor chip 20 may be encapsulated with an epoxy resin composition 40, and the epoxy resin composition may be the epoxy resin composition according to embodiments of the present invention.

Figure 3:
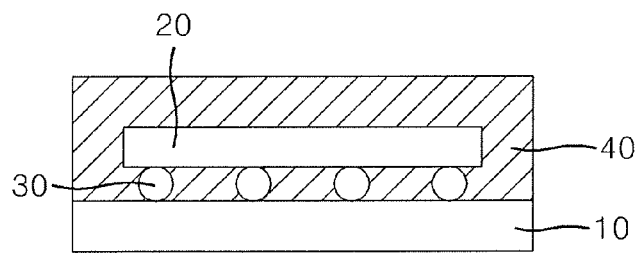
FIG. 3 is a sectional view of a semiconductor device according to another embodiment of the present invention.

FIG. 3 is a sectional view of a semiconductor device according to another embodiment of the present invention. Referring to FIG. 3, a semiconductor device 200 according to another embodiment includes a wiring board 10, bumps 30 formed on the wiring board 10, and a semiconductor chip 20 formed on the bumps 30, wherein a gap between the wiring board 10 and the semiconductor chip 20 and the entirety of a top surface of the semiconductor chip 20 may be encapsulated with an epoxy resin composition 40, and the epoxy resin composition may be the epoxy resin composition according to embodiments of the present invention.

In FIGS. 2 to 3, the size of each wiring board, bump and semiconductor chip, and the numbers of the bumps are optional and may be modified.

MODE FOR INVENTION

Next, the present invention will be described in more detail with reference to some examples. It should be understood that these examples are provided for illustration only and are not to be construed in any way as limiting the present invention.

Example 1

0.79 g of pyridine and 2.2 g of 4-methoxybenzyl bromide were dissolved in 20 ml of toluene, followed by reacting at 100° C. for 3 hours and then filtering and drying a produced precipitate, thereby obtaining 2.79 g of a solid. 2.79 g of the obtained solid was dissolved in 50 ml of methylene chloride, followed by reacting with 1.90 g of sodium diethyldithiocarbamate at 25° C. for 24 hours and then filtering a produced precipitate to obtain a liquid, which in turn was subjected to distillation under reduced pressure (evaporating), thereby obtaining 3.48 g of a solid represented by Formula 7:

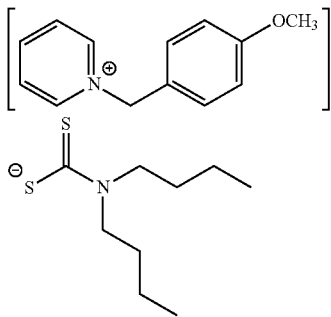

$^1$H NMR (400 MHz, DMSO) 8.70 (d, J=4.8 Hz, 2H), 8.48 (t, J=8.0 Hz, 1H), 7.99 (t, J=7.0 Hz, 2H), 7.40 (d, J=9.0 Hz, 2H), 6.99 (d, J=9.0 Hz, 2H), 5.62 (s, 2H), 4.05 (q, J=7.4 Hz, 4H), 3.79 (s, 3H), 1.20 (t, J=7.4 Hz, 6H) ppm; $^{13}$C NMR (100 MHz, DMSO) 207.3, 157.7, 146.2, 146.0, 130.1, 128.5, 126.8, 114.2, 62.1, 55.0, 48.0, 12.7 ppm; LC-MS m/z=348 (M$^+$); Anal. Calcd for $C_{18}H_{24}N_2OS_2$: C, 62.03; H, 6.94; N, 8.04; S, 18.40. Found: C, 62.14; H, 6.56; N, 8.43; S, 18.84.

Example 2

0.79 g of pyridine and 2.2 g of 4-methoxybenzyl bromide were dissolved in 20 ml of toluene, followed by reacting at 100° C. for 3 hours and then filtering and drying a produced precipitate, thereby obtaining 2.79 g of a solid. 2.79 g of the obtained solid was dissolved in 50 ml of methylene chloride, followed by reacting with 2.3 g of sodium dibutyldithiocarbamate at 25° C. for 24 hours and then filtering a produced precipitate to obtain a liquid, which in turn was subjected to distillation under reduced pressure (evaporating), thereby obtaining 4.0 g of a solid represented by Formula 8:

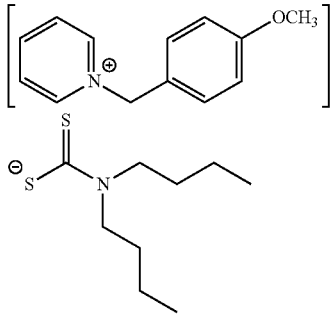

$^1$H NMR (400 MHz, DMSO) 8.71 (d, J=4.8 Hz, 2H), 8.49 (t, J=7.8 Hz, 1H), 8.0 (t, J=7.0 Hz, 2H), 7.40 (d, J=9.0 Hz, 2H), 6.99 (d, J=9.0 Hz, 2H), 5.60 (s, 2H), 3.80 (s, 3H), 2.55 (t, J=7.2 Hz, 4H), 1.45-1.30 (m, 8H) 0.96 (t, J=7.2 Hz, 6H) ppm; $^{13}$C NMR (100 MHz, DMSO) 207.1, 157.6, 146.5, 146.1, 130.1, 128.2, 126.5, 114.0, 62.1, 55.1, 54.1, 29.8, 20.2, 13.8 ppm; LC-MS m/z=404 (M$^+$); Anal. Calcd for $C_{22}H_{32}N_2OS_2$: C, 65.30; H, 7.97; N, 6.92; S, 15.85. Found: C, 65.35; H, 7.99; N, 6.58; S, 15.67.

Example 3

0.79 g of pyridine and 2.2 g of 4-methoxybenzyl bromide were dissolved in 20 ml of toluene, followed by reacting at 100° C. for 3 hours and then filtering and drying a produced precipitate, thereby obtaining 2.79 g of a solid. 2.79 g of the obtained solid was dissolved in 50 ml of methylene chloride, followed by reacting with 3.0 g of sodium dibenzyldithiocarbamate at 25° C. for 24 hours and then filtering a produced precipitate to obtain a liquid, which in turn was subjected to distillation under reduced pressure (evaporating), thereby obtaining 4.7 g of a solid represented by Formula 9:

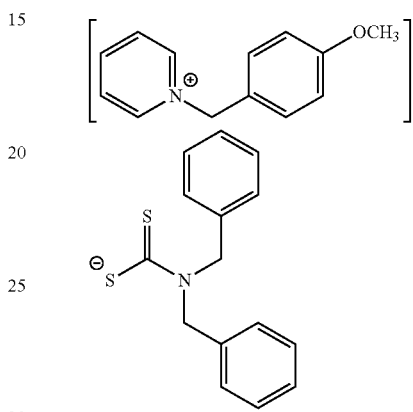

$^1$H NMR (400 MHz, DMSO) 8.72 (d, J=4.8 Hz, 2H), 8.49 (t, J=8.0 Hz, 1H), 7.98 (t, J=7.0 Hz, 2H), 7.38 (d, J=9.0 Hz, 2H), 7.15-7.05 (m, 10H), 7.01 (d, J=9.0 Hz, 2H), 5.60 (s, 2H), 4.05 (q, J=7.4 Hz, 4H), 3.84 (s, 2H), 3.76 (s, 3H) ppm; $^{13}$C NMR (100 MHz, DMSO) 208.3, 157.7, 146.2, 146.0, 136.5, 130.1, 128.6, 128.5, 128.0, 127.1, 126.8, 114.2, 62.1, 56.7, 55.9 ppm; LC-MS m/z=472 (M$^+$); Anal. Calcd for $C_{28}H_{28}N_2OS_2$: C, 71.15; H, 5.97; N, 5.93; S, 13.57. Found: C, 62.14; H, 6.56; N, 8.43; S, 18.84.

Example 4

1.04 g of 4-cyanopyridine and 2.2 g of 4-methoxybenzyl bromide were dissolved in 20 ml of toluene, followed by reacting at 100° C. for 3 hours and then filtering and drying a produced precipitate, thereby obtaining 3.04 g of a solid. 3.04 g of the obtained solid was dissolved in 50 ml of methylene chloride, followed by reacting with 1.90 g of sodium diethyldithiocarbamate at 25° C. for 24 hours and then filtering a produced precipitate to obtain a liquid, which in turn was subjected to distillation under reduced pressure (evaporating), thereby obtaining 3.70 g of a solid represented by Formula 10:

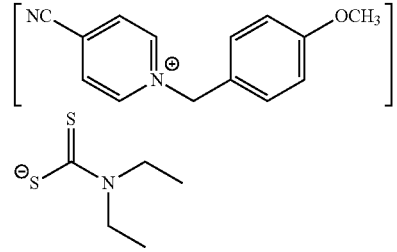

$^1$H NMR (400 MHz, DMSO) 9.70 (d, J=7.2 Hz, 2H), 9.13 (d, J=7.2 Hz, 2H), 6.95 (d, J=9.0 Hz, 2H), 6.65 (d, J=9.0 Hz, 2H), 5.62 (s, 2H), 4.05 (q, J=7.4 Hz, 4H), 3.79 (s, 3H), 1.18 (t, J=7.4 Hz, 6H) ppm; $^{13}$C NMR (100 MHz, DMSO) 207.3, 157.7, 148.1, 117.0, 130.4, 126.4, 62.1, 126.8, 130.1, 114.2, 48.2, 12.6 ppm; LC-MS m/z=373 (M$^+$); Anal. Calcd for $C_{19}H_{23}N_3OS_2$: C, 61.09; H, 6.21; N, 11.25; S, 17.17. Found: C, 61.32; H, 6.33; N, 11.46; S, 17.52.

Example 5

1.04 g of 4-cyanopyridine and 2.3 g of 4-nitrobenzyl bromide were dissolved in 20 ml of toluene, followed by reacting at 100° C. for 3 hours and then filtering and drying a produced precipitate, thereby obtaining 3.19 g of a solid. 3.19 g of the obtained solid was dissolved in 50 ml of methylene chloride, followed by reacting with 1.90 g of sodium diethyldithiocarbamate at 25° C. for 24 hours and then filtering a produced precipitate to obtain a liquid, which in turn was subjected to distillation under reduced pressure (evaporating), thereby obtaining 3.88 g of a solid represented by Formula 11:

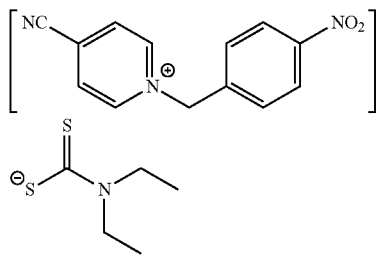

$^1$H NMR (400 MHz, DMSO) 9.70 (d, 1=7.2 Hz, 2H), 9.10 (d, J=7.2 Hz, 2H), 8.07 (d, J=9.0 Hz, 2H), 7.32 (d, J=9.0 Hz, 2H), 5.60 (s, 2H), 2.59 (q, J=7.4 Hz, 4H), 1.01 (t, J=7.4 Hz, 6H) ppm; $^{13}$C NMR (100 MHz, DMSO) 207.4, 148.1, 145.4, 140.6, 130.4, 130.0, 126.4, 121.0, 117.0, 62.1, 48.1, 12.5 ppm; LC-MS m/z=388 (M$^+$); Anal. Calcd for $C_{18}H_{20}N_4O_2S_2$: C, 55.65; H, 5.19; N, 14.42; S, 16.51. Found: C, 55.63; H, 5.19; N, 14.46; S, 16.93.

Example 6

0.79 g of pyridine and 2.2 g of 4-methoxybenzyl bromide were dissolved in 20 ml of toluene, followed by reacting at 100° C. for 3 hours and then filtering and drying a produced precipitate, thereby obtaining 2.79 g of a solid. 2.79 g of the obtained solid was dissolved in 50 ml of methylene chloride, followed by reacting with 1.6 g of sodium isopropylxanthate at 25° C. for 24 hours and then filtering a produced precipitate to obtain a liquid, which in turn was subjected to distillation under reduced pressure (evaporating), thereby obtaining 3.35 g of a solid represented by Formula 12:

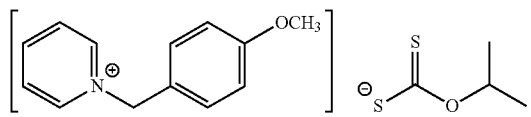

$^1$H NMR (400 MHz, DMSO) 8.68 (d, J=4.8 Hz, 2H), 8.46 (t, J=8.0 Hz, 1H), 7.95 (t, J=7.0 Hz, 2H), 7.42 (d, J=9.0 Hz, 2H), 7.01 (d, J=9.0 Hz, 2H), 5.62 (s, 2H), 3.57 (q, J=7.2 Hz, 4H), 1.16 (d, J=7.2 Hz, 6H) ppm; $^{13}$C NMR (100 MHz, DMSO) 184.3, 157.8, 146.4, 146.1, 130.2, 128.6, 126.7, 114.2, 62.1, 55.1, 70.1, 24.2 ppm; LC-MS m/z=335 (M$^+$); Anal. Calcd for $C_{17}H_{21}NO_2S_2$: C, 60.86; H, 6.31; N, 4.18; S, 19.12. Found: C, 60.76; H, 6.16; N, 4.49; S, 19.54.

Example 7

8.5 parts by weight of a biphenyl type epoxy resin (NC-3000, Nippon Kayaku), 5.2 parts by weight of a xyloc type phenol resin (HE100C-10, Air Water), 0.3 parts by weight of the compound in Example 1, 85 parts by weight of inorganic fillers obtained by mixing spherical fused silica having an average particle diameter of 18 μm with spherical fused silica having an average particle diameter of 0.5 μm in a weight ratio of 9:1, 0.4 parts by weight of a coupling agent obtained by mixing 0.2 parts by weight of mercaptopropyltrimethoxysilane (KBM-803, Shin Etsu Co., Ltd.) with 0.2 parts by weight of methyltrimethoxysilane (SZ-6070, Dow Corning Chemical Co., Ltd.), 0.3 parts by weight of carnauba wax as a release agent, and 0.3 parts by weight of Carbon black (MA-600, Matsushita Chemical Co., Ltd.) as a coloring agent were mixed, followed by uniformly stirring using a Henschel mixer, thereby obtaining a powdery composition. Then, the obtained powder was subjected to melt kneading using a continuous kneader at 95° C., followed by cooling and pulverizing, thereby preparing an epoxy resin composition for encapsulating a semiconductor device.

Example 8 to 12

Epoxy resin compositions for encapsulating a semiconductor device were prepared in the same manner as in Example 7 except that compounds listed in Table 1 (unit: parts by weight) were used instead of the compound in Example 1.

Comparative Example 1

An epoxy resin composition for encapsulating a semiconductor device was prepared in the same manner as in Example 7 except that a compound represented by Formula 13 (2MZ, SAN-APRO) was used instead of the compound in Example 1.

<Formula 13>

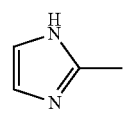

Comparative Example 2

An epoxy resin composition for encapsulating a semiconductor device was prepared in the same manner as in Example 7 except that a compound represented by Formula 14 (2P4MHZ-PW, Nippon-Gosei) was used instead of the compound in Example 1.

<Formula 14>

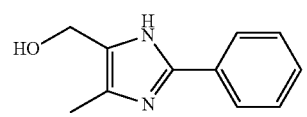

Comparative Example 3

An epoxy resin composition for encapsulating a semiconductor device was prepared in the same manner as in Example 7 except that a $BF_4^-$ anion-containing compound represented by Formula 14 (1,3-Di-tert-butylimidazolium tetrafluoroborate, Sigma-Aldrich) was used instead of the compound in Example 1.

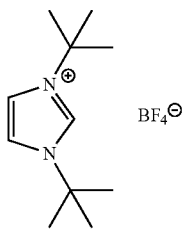

<Formula 15> molding curing (PMC) in an oven at 170° C. to 180° C. for 4 hours and left at 85° C. and 85% RH for 168 hours, followed by measuring a weight change of the specimen due to moisture absorption, thereby calculating a moisture absorption rate according to Equation 3:

Moisture absorption rate (%)=(Weight of specimen after moisture absorption−Weight of specimen before moisture absorption)÷(Weight of specimen before moisture absorption)×100  <Equation 3>

(4) Adhesive strength (kgf): A copper metal device having a size adapted to a mold for adhesive strength measurement was prepared as a test piece. Each of the resin compositions prepared in Examples and Comparative Examples was molded on the test piece at a mold temperature of 170° C. to 180° C., a clamp pressure of 70 kgf/cm², a transfer pressure of 1,000 psi, and a transfer speed of 0.5 cm/s to 1 cm/s for a curing time of 120 sec to obtain a cured specimen. The specimen was subjected to post-molding curing (PMC) in an oven at 170° C. to 180° C. for 4 hours. The area of the epoxy resin composition in contact with the specimen was 40±1 mm², and the adhesive strength of the epoxy resin

TABLE 1

| Component | | Example | | | | | | Comparative Example | | |
|---|---|---|---|---|---|---|---|---|---|---|
| | | 7 | 8 | 9 | 10 | 11 | 12 | 1 | 2 | 3 |
| Epoxy resin | | 8.5 | 8.5 | 8.5 | 8.5 | 8.5 | 8.5 | 8.5 | 8.5 | 8.5 |
| Curing agent | | 5.2 | 5.2 | 5.2 | 5.2 | 5.2 | 5.2 | 5.2 | 5.2 | 5.2 |
| Curing catalyst | Example 1 | 0.3 | — | — | — | — | — | — | — | — |
| | Example 2 | — | 0.3 | — | — | — | — | — | — | — |
| | Example 3 | — | — | 0.3 | — | — | — | — | — | — |
| | Example 4 | — | — | — | 0.3 | — | — | — | — | — |
| | Example 5 | — | — | — | — | 0.3 | — | — | — | — |
| | Example 6 | — | — | — | — | — | 0.3 | — | — | — |
| | Formula 13 | — | — | — | — | — | — | 0.3 | — | — |
| | Formula 14 | — | — | — | — | — | — | — | 0.3 | — |
| | Formula 15 | — | — | — | — | — | — | — | — | 0.3 |
| Inorganic filler | | 85 | 85 | 85 | 85 | 85 | 85 | 85 | 85 | 85 |
| Coupling agent | KBM-803 | 0.2 | 0.2 | 0.2 | 0.2 | 0.2 | 0.2 | 0.2 | 0.2 | 0.2 |
| | SZ-6070 | 0.2 | 0.2 | 0.2 | 0.2 | 0.2 | 0.2 | 0.2 | 0.2 | 0.2 |
| Release agent | | 0.3 | 0.3 | 0.3 | 0.3 | 0.3 | 0.3 | 0.3 | 0.3 | 0.3 |
| Coloring agent | | 0.3 | 0.3 | 0.3 | 0.3 | 0.3 | 0.3 | 0.3 | 0.3 | 0.3 |

The epoxy resin compositions prepared in Examples 7 to 12 and Comparative Examples were evaluated as to physical properties by way of the following measurement methods. Results are summarized in Table 2 and FIG. 4.

(1) Flowability (inches): The flow length of each of the epoxy resin compositions was measured using a transfer molding press in a test mold at 175° C. and 70 kgf/cm² in accordance with EMMI-1-66. A higher measured value indicates better flowability.

(2) Glass transition temperature (° C.): Glass transition temperature was measured using a thermomechanical analyzer (TMA) while heating at a rate of 10° C./min from 25° C. to 300° C.

(3) Moisture absorption rate (%): Each of the epoxy resin compositions was molded at a mold temperature of 170° C. to 180° C., a clamp pressure of 70 kg/cm², a transfer pressure of 1,000 psi, and a transfer speed of 0.5 cm/s to 1 cm/s for a curing time of 120 sec to obtain a cured specimen in the form of a disc having a diameter of 50 mm and a thickness of 1.0 mm. The specimen was subjected to postcomposition was measured with respect to 12 specimens in each measurement process using a universal testing machine (UTM) and the measured adhesive strength values were averaged.

(5) Degree of cure (Shore-D): Each of the epoxy resin compositions was cured using a multi plunger system (MPS) equipped with a mold at 175° C. for 50 sec, 60 sec, 70 sec, 80 sec, and 90 sec to construct exposed thin quad flat packages (eTQFPs), each including a copper metal device having a width of 24 mm, a length of 24 mm and a thickness of 1 mm. Hardness of the cured products in the packages on the mold according to the curing periods of time were directly measured using a Shore D durometer. A higher hardness value indicates better degree of cure.

(6) Storage stability (%): The flow length of each of the epoxy resin compositions was measured in accordance with the method described in (1) while storing the compositions for one week in a thermo-hygrostat set to 25° C./50% RH at an interval of 24 hours. Percent (%) of the flow length after storage to the flow length immediately after preparation of the composition was calculated. A higher value indicates better storage stability.

(7) Differential Scanning calorimeter (DSC) measurement: A differential scanning calorimeter is an instrument which shows difference in heat flow between a sample and an inert reference as a function of temperature while changing the temperature of the sample and the inert reference according to the same temperature program, and can trace heat capacity and time-dependent heat flow of a sample to be measured using the heating rate input according to a preset temperature program and thermal signals of DSC to measure curing initiation temperature, curing rate at a curing temperature, and reaction energy.

DSC initial start temperature: After maintaining a specimen of each of the epoxy resin compositions at 30° C. for 1 min, the specimen was heated to 250° C. at a rate of 10° C./min, followed by measurement of curing rate, hardness, and reaction energy. Here, the curing initiation temperature refers to a temperature at which the inclination of the heat of reaction curve at the peak temperature meets a line connecting the temperature at which curing of the specimen starts and the temperature at which curing of the specimen is complete.

(8) Rate of viscosity change: Viscosity of each of the epoxy resin compositions was measured at 25° C., and viscosity of each of the epoxy resin compositions was measured at 25° C. after leaving the epoxy resin compositions at 25° C. for 24 hours, followed by calculating rate of viscosity change according to Equation 1. Viscosity was measured using a coaxial double cylinder type rotary viscometer (PM-2 A, Malcomtech International). A lower rate of viscosity change indicates that the epoxy resin composition was less cured and thus exhibited high storage stability.

$$\text{Rate of change in viscosity} = |B-A|/A \times 100 \qquad \text{<Equation 1>}$$

(where A is the viscosity (unit: cPs) of the epoxy resin composition as measured at 25° C., and B is the viscosity (unit: cPs) of the epoxy resin composition as measured at 25° C. after leaving the epoxy resin composition at 25° C. for 24 hours).

TABLE 2

Figure 4:
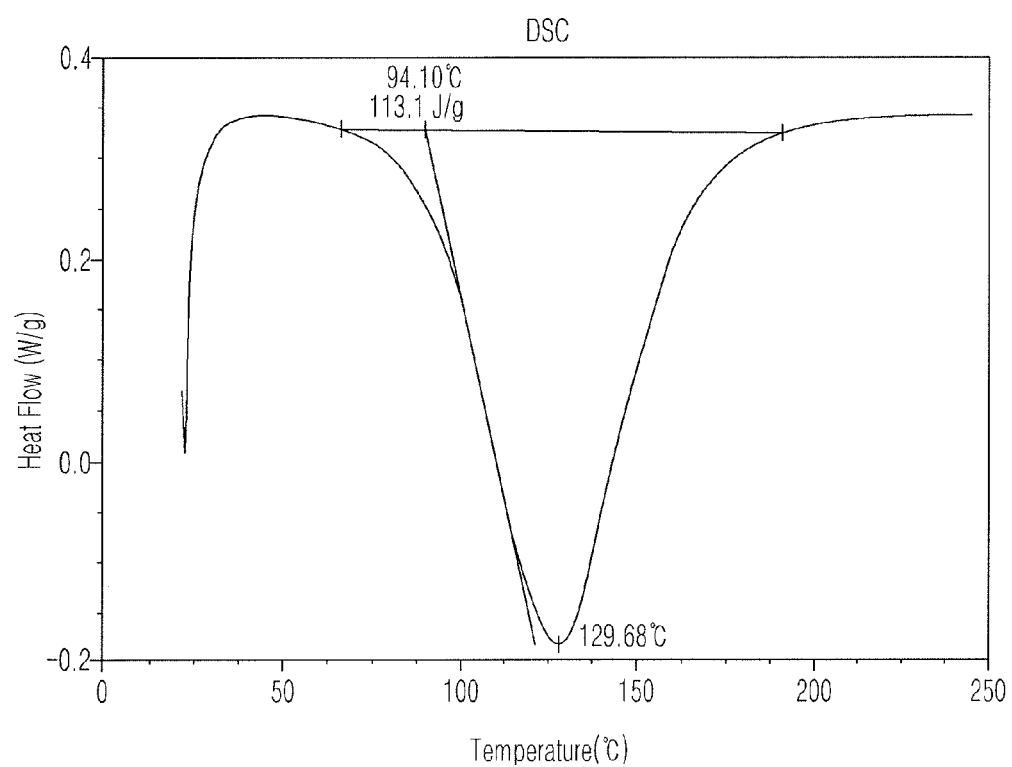
FIG. 4 is a view showing results of differential scanning calorimetry (DSC) analysis of an epoxy resin composition of Example 1.

| | Evaluation item | | Example | | | | | | Comparative Example | | |
|---|---|---|---|---|---|---|---|---|---|---|---|
| | | | 7 | 8 | 9 | 10 | 11 | 12 | 1 | 2 | 3 |
| Basic physical properties | Flowability (inch) | | 68 | 70 | 72 | 68 | 69 | 70 | 40 | 62 | 58 |
| | Glass transition temperature (° C.) | | 148 | 147 | 147 | 145 | 145 | 146 | 154 | 148 | 154 |
| | Moisture absorption (%) | | 0.32 | 0.31 | 0.32 | 0.31 | 0.30 | 0.32 | 0.39 | 0.36 | 0.36 |
| | Adhesive strength (kgf) | | 77 | 74 | 74 | 74 | 75 | 75 | 72 | 74 | 72 |
| | Curing initiation temperature (° C.) | | 94.10 | 95 | 96 | 92 | 94 | 93 | 105 | 110 | 124 |
| | Width of curing temperature range (° C.) | | 59 | 62 | 57 | 61 | 55 | 63 | 93 | 87 | 104 |
| | Rate of viscosity change (%) | | 8.1 | 7.8 | 7.9 | 8.2 | 7.9 | 7.8 | 15.2 | 27.3 | 13.8 |
| Evaluation of packages | Degree of cure (Shore-D) according to curing time | 50 sec | 67 | 66 | 68 | 69 | 69 | 70 | 52 | 52 | 53 |
| | | 60 sec | 71 | 69 | 70 | 71 | 72 | 72 | 63 | 57 | 58 |
| | | 70 sec | 72 | 74 | 72 | 72 | 73 | 73 | 70 | 62 | 63 |
| | | 80 sec | 73 | 76 | 75 | 74 | 75 | 74 | 73 | 68 | 68 |
| | | 90 sec | 74 | 76 | 78 | 75 | 77 | 74 | 74 | 68 | 68 |
| | Storage stability (%) | 24 hr | 95 | 96 | 97 | 98 | 99 | 98 | 82 | 92 | 91 |
| | | 48 hr | 91 | 92 | 94 | 95 | 96 | 95 | 66 | 84 | 85 |
| | | 72 hr | 88 | 88 | 90 | 92 | 93 | 92 | 44 | 80 | 78 | ing the temperature at which curing of the specimen starts and the temperature at which curing of the specimen is complete, and the width of curing temperature range refers to a difference between the temperature at which curing of the specimen starts and the temperature at which curing of the specimen is complete. Referring to FIG. 4, for the composition in Example 1, the curing initiation temperature is 94.10° C., at which the inclination of the heat of reaction curve at 129.68° C. corresponding to the peak temperature meets the line (shown as a straight line) connecting the temperature at which curing of the specimen starts and the temperature at which curing of the specimen is complete.

As shown in Table 2, it could be seen that the epoxy resin compositions for encapsulating a semiconductor device according to the present invention had low curing initiation temperature and narrow curing temperature range, thereby exhibiting enhanced processability and productivity. In addition, the epoxy resin compositions according to the present invention had low rate of viscosity change and showed less change in flowability after 72 hours, thereby exhibiting high storage stability.

On the contrary, the compositions prepared in Comparative Examples 1 and 2 including the imidazole catalyst had low rate of viscosity change, low storage stability, and high moisture absorption, and the composition prepared in Comparative Example 3 including fluorine ions as anions had high curing initiation temperature.

It should be understood that various modifications, changes, alterations, and equivalent embodiments can be made by those skilled in the art without departing from the spirit and scope of the invention.

The invention claimed is:

1. A pyridinium-based compound represented by Formula 1:

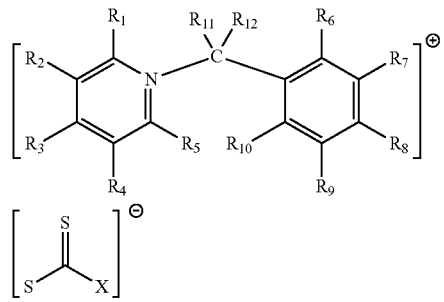

<Formula 1>

(wherein, in Formula 1, $R_1$, $R_2$, $R_3$, $R_4$, $R_5$, $R_6$, $R_7$, $R_8$, $R_9$, and $R_{10}$ are each independently hydrogen, a hydroxyl group, an amino group (—$NH_2$), a nitro group (—$NO_2$), a cyano group (—CN), a $C_1$ to $C_{10}$ alkyl group, a $C_6$ to $C_{20}$ aryl group, a $C_1$ to $C_{10}$ alkoxy group, a $C_3$ to $C_{10}$ cycloalkyl group, R—C(=O)—* (where R is a $C_1$ to $C_{10}$ alkyl group, and * is a binding site between elements), or R'—$SO_2$—* (where * is a binding site between elements, and R' is a $C_1$ to $C_{10}$ alkyl group or $C_6$ to $C_{20}$ aryl group);

$R_{11}$ and $R_{12}$ are each independently hydrogen, a $C_1$ to $C_{10}$ alkyl group, a $C_6$ to $C_{20}$ aryl group, or a hydroxyl group; and X is *—$NR_aR_b$ (where $R_a$ and $R_b$ are each independently hydrogen, a $C_1$ to $C_{10}$ alkyl group, a $C_6$ to $C_{20}$ aryl group, a $C_1$ to $C_{10}$ alkoxy group, a $C_6$ to $C_{20}$ aryloxy group, or a $C_7$ to $C_{20}$ arylalkyl group, and * is a binding site between elements) or *—$OR_c$ (where $R_c$ is hydrogen, a $C_1$ to $C_4$ alkyl group, a $C_6$ to $C_{20}$ aryl group, a $C_1$ to $C_{10}$ alkoxy group, a $C_6$ to $C_{20}$ aryloxy group, or a $C_7$ to $C_{20}$ arylalkyl group, and * is a binding site between elements).

2. The pyridinium-based compound according to claim 1, wherein the pyridinium-based compound is represented by any one of Formulas 7 to 12:

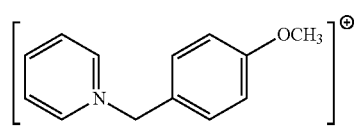

<Formula 7>

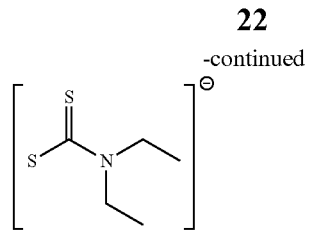

<Formula 8>

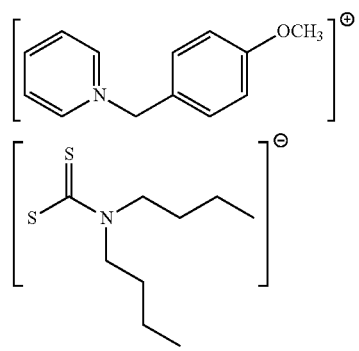

<Formula 9>

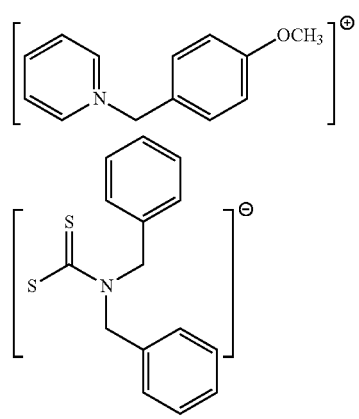

<Formula 10>

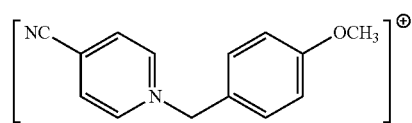
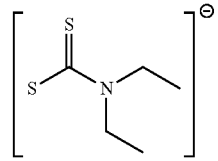

<Formula 11>

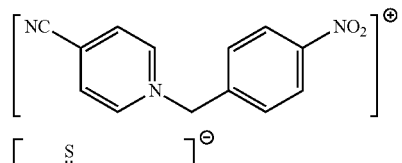
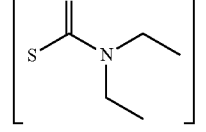

<Formula 12>

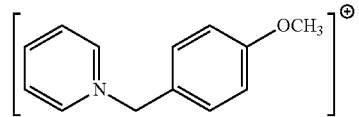

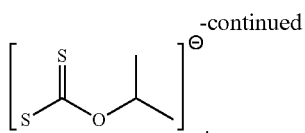

3. A curing catalyst represented by Formula 1:

<Formula 1>

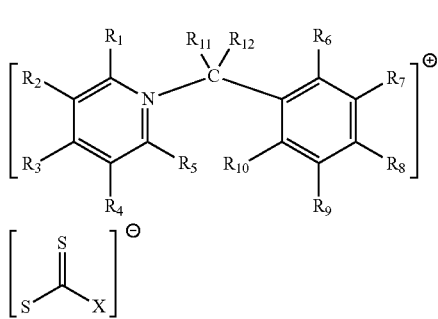

(wherein, in Formula 1, $R_1$, $R_2$, $R_3$, $R_4$, $R_5$, $R_6$, $R_7$, $R_8$, $R_9$, and $R_{10}$ are each independently hydrogen, a hydroxyl group, an amino group (—$NH_2$), a nitro group (—$NO_2$), a cyano group (—CN), a $C_1$ to $C_{10}$ alkyl group, a $C_6$ to $C_{20}$ aryl group, a $C_1$ to $C_{10}$ alkoxy group, a $C_3$ to $C_{10}$ cycloalkyl group, R—C(=O)—* (where R is a $C_1$ to $C_{10}$ alkyl group, and * is a binding site between elements), or R'—$SO_2$—* (where * is a binding site between elements, and R' is a $C_1$ to $C_1$ alkyl group or $C_6$ to $C_{20}$ aryl group);

$R_{11}$ and $R_{12}$ are each independently hydrogen, a $C_1$ to $C_{10}$ alkyl group, a $C_6$ to $C_{20}$ aryl group, or a hydroxyl group; and X is *—$NR_aR_b$ (where $R_a$ and $R_b$ are each independently hydrogen, a $C_1$ to $C_{10}$ alkyl group, a $C_6$ to $C_{20}$ aryl group, a $C_1$ to $C_{10}$ alkoxy group, a $C_6$ to $C_{20}$ aryloxy group, or a $C_7$ to $C_{20}$ arylalkyl group, and * is a binding site between elements) or *—$OR_c$ (where $R_c$ is hydrogen, a $C_1$ to $C_4$ alkyl group, a $C_6$ to $C_{20}$ aryl group, a $C_1$ to $C_{10}$ alkoxy group, a $C_6$ to $C_{20}$ aryloxy group, or a $C_7$ to $C_{20}$ arylalkyl group, and * is a binding site between elements).

4. An epoxy resin composition, comprising:
an epoxy resin, a curing agent, and a curing catalyst, wherein the curing catalyst includes the pyridinium-based compound according to claim 1.

5. The epoxy resin composition according to claim 4, wherein the epoxy resin includes an epoxy resin having two or more epoxy groups and one or more hydroxyl groups per molecule.

6. The epoxy resin composition according to claim 4, wherein the curing agent includes a phenol resin.

7. The epoxy resin composition according to claim 4, wherein the pyridinium-based compound is present in an amount of about 0.01 wt % to about 5 wt % in the epoxy resin composition.

8. The epoxy resin composition according to claim 4, wherein the pyridinium-based compound is present in an amount of about 10 wt % to about 100 wt % in the curing catalyst.

9. The epoxy resin composition according to claim 4, further comprising an inorganic filler.

10. The epoxy resin composition according to claim 9, comprising: about 2 wt % to about 17 wt % of the epoxy resin; about 0.5 wt % to about 13 wt % of the curing agent; about 70 wt % to about 95 wt % of the inorganic filler; and about 0.01 wt % to about 5 wt % of the curing catalyst.

11. An epoxy resin composition for encapsulating a semiconductor device comprising the epoxy resin composition according to claim 4.

12. An apparatus manufactured using the epoxy resin composition according to claim 4.

* * * * *

UNITED STATES PATENT AND TRADEMARK OFFICE
CERTIFICATE OF CORRECTION

PATENT NO. : 9,957,348 B2
APPLICATION NO. : 15/111337
DATED : May 1, 2018
INVENTOR(S) : Dong Hwan Lee et al.

It is certified that error appears in the above-identified patent and that said Letters Patent is hereby corrected as shown below:

On the Title Page

Item (54) Title:
First word "PYRIDINIUIVI"
Should read:
"PYRIDINIUM"

Item (30) Foreign Application Priority Data:
"10-2014-004794"
Should read:
"10-2014-0004794"

Signed and Sealed this
Fourth Day of June, 2019

Andrei Iancu
*Director of the United States Patent and Trademark Office*